United States Patent [19]
Levinson et al.

[11] Patent Number: 5,960,610
[45] Date of Patent: Oct. 5, 1999

[54] METHOD OF CURVING A FETAL SENSOR

[75] Inventors: Mitchell Levinson, Pleasanton; James R. Casciani, Cupertino; Bryan J. Weber, Livermore; Daniel Gronvall, Pleasanton; Phillip S. Palmer, San Leandro; Andres Jimenez Lopez, Tijuana; Richard L. Shaw, Morgan Hill, all of Calif.

[73] Assignee: Nellcor Puritan Bennett Incorporated, Pleasanton, Calif.

[21] Appl. No.: 08/941,947

[22] Filed: Oct. 1, 1997

[51] Int. Cl.⁶ .............................. B65B 23/00; B65B 63/04
[52] U.S. Cl. .................... 53/429; 53/410; 53/472
[58] Field of Search ................ 53/410, 429, 430, 53/139.5, 472, 474, 445

[56] References Cited

U.S. PATENT DOCUMENTS

| | | | |
|---|---|---|---|
| 3,839,841 | 10/1974 | Amplatz | 53/429 |
| 5,129,514 | 7/1992 | Lilley | 53/530 |
| 5,209,042 | 5/1993 | Rickard | 53/430 |
| 5,228,565 | 7/1993 | Sinn | 53/430 |
| 5,247,932 | 9/1993 | Chung et al. | 128/633 |
| 5,261,210 | 11/1993 | Brown | 53/429 |
| 5,377,675 | 1/1995 | Ruskewicz et al. | 128/634 |
| 5,497,601 | 3/1996 | Gonzalez | 53/450 |

*Primary Examiner*—Linda Johnson
*Attorney, Agent, or Firm*—Townsend and Townsend and Crew LLP

[57] ABSTRACT

An improved method for bending an oximeter sensor which simplifies the manufacturing. The sensor is manufactured without a bend, but when it is packaged for shipping, it is bent and restrained in the bent position. The sensor is made of a material which has memory so that when the packaging which restrains it is removed for use, the sensor will retain a partially bent shape.

11 Claims, 3 Drawing Sheets

METHOD OF CURVING A FETAL SENSOR

BACKGROUND OF THE INVENTION

The present invention relates to oximeter sensors, in particular a fetal pulse oximetry intrauterine sensor.

Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor which scatters light through a portion of the patient's tissue where blood perfuses the tissue, and photoelectrically senses the absorption of light in such tissue. The amount of light absorbed is then used to calculate the amount of blood constituent being measured.

The light scattered through the tissue is selected to be of one or more wavelengths that are absorbed by the blood in an amount representative of the amount of the blood constituent present in the blood. The amount of transmitted light scattered through the tissue will vary in accordance with the changing amount of blood constituent in the tissue and the related light absorption. For measuring blood oxygen level, such sensors have been provided with light sources and photodetectors that are adapted to operate at two different wavelengths, in accordance with known techniques for measuring blood oxygen saturation.

Known non-invasive sensors include devices that are secured to a portion of the body, such as a finger, ear or the scalp. In animals and humans, the tissue of these body portions is perfused with blood and the tissue surface is readily accessible to the clinician.

It is desirable that photoelectric pulse oximetry also be useful for monitoring the blood characteristics and constituents of a fetus. For example, monitoring fetal oxygen levels provides an effective way to detect and provide indications for treating hypoxia in the fetus during labor.

A number of different designs are used for fetal sensors. U.S. Pat. No. 5,247,932 shows a bladder between the fetus and the uterine wall which presses the active face of the sensor against the fetus' skin. U.S. Pat. No. 5,377,675 discloses a sensor using a fulcrum to bias the sensor against the fetus. PCT Published Application No. W091/07910 uses an inflatable sac to wedge the sensor against the fetus.

FIG. 1 illustrates the insertion of a fetal pulse oximeter sensor into a uterus so that a sensor portion 10 is against the head of a fetus 12. The sensor 10, or sensor head, is connected to a sensor rod 14 which extends out of the uterus. It is desirable to have this rod bend to go around the side of the fetus' head. In one type of sensor, the sensor rod is made by an extrusion process, which does not allow a bent shape. The sensor head is attached and sealed with an overmold, which may be shaped to produce a fulcrum as shown in U.S. Pat. No. 5,377,675.

U.S. Pat. No. 5,247,932 is one example of using a stylet to allow insertion of a sensor and then the subsequent bending needed. The sensor rod is made by a process which allows it to be preformed to be bent, and the metal stylet is inserted into a channel in the sensor rod to straighten it for insertion. After being inserted, the metal stylet is removed so that the sensor rod returns to its original bent shape, biasing the sensor against the fetus. Typically, the sensor rod is manufactured to be bent. One way to manufacture this way is to extrude the rod, then insert a permanent stylet which is curved. A separate lumen is provided for the metal stylet which will straighten the sensor for insertion.

SUMMARY OF THE INVENTION

The present invention provides an improved method for bending an oximeter sensor which simplifies the manufacturing. The sensor is manufactured without a bend, but when it is packaged for shipping, it is bent and restrained in the bent position. The sensor is made of a material which has memory so that when the packaging which restrains it is removed for use, the sensor will retain a partially bent shape.

In one embodiment, the sensor is bent around a 180° angle and the sensor head of the sensor is tied, clipped, or otherwise secured to the sensor rod. Alternately, a sleeve could be used, which would enclose a portion of the sensor rod and the sensor head or below the sensor head. In another embodiment, the sensor is bent and then inserted in packaging narrow enough to prevent the sensor rod from unbending. Alternately, the packaging may be specially shaped to be narrower, or a preformed tray having a formed bend could be used in which to insert the sensor.

In an alternate embodiment, a curve is manufactured into the sensor by extending the overmold material used for the sensor head over a portion of the sensor rod. Since the sensor head overmold is typically made by molding, rather than by extrusion as for a sensor rod, it can be molded with a curve over a distance sufficient to partially wrap around a fetus' head.

In yet another embodiment, a special, curved stylet is inserted into the sensor rod to bend it. When the sensor is prepared for use, the bent stylet is removed and discarded, with the sensor rod retaining the bent shape. A normal stylet can then be used as in the prior art to straighten the sensor rod temporarily for insertion, and then can be removed to allow the sensor rod to return to its bent shape to bias the sensor against the fetus.

For a further understanding of the nature and advantages of the invention, reference should be made to the following description taken in conjunction with the accompanying drawings.

DESCRIPTION OF THE PREFERRED EMBODIMENT

Figure 1:
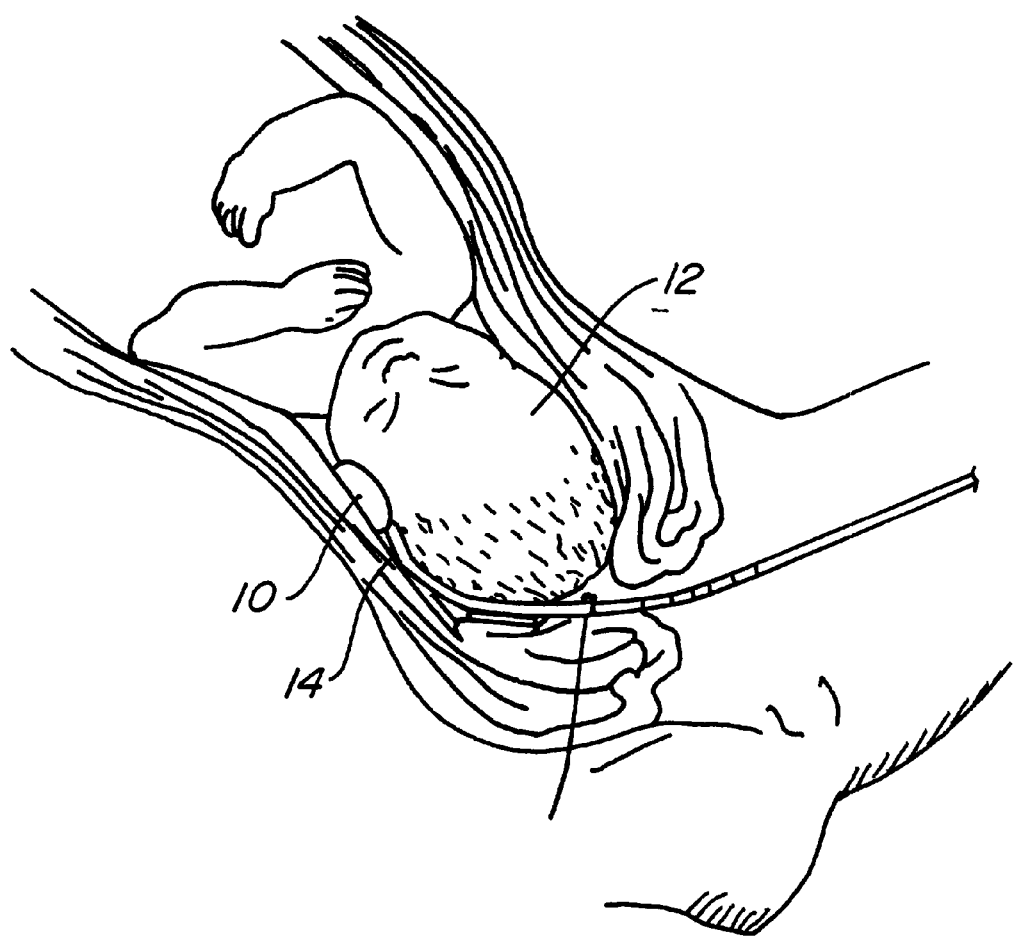
FIG. 1 is a diagram of a fetal sensor in use curved around a fetus' head.
Figure 2A:
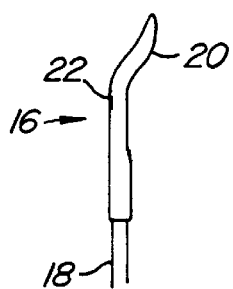
FIGS. 2A–2C illustrate one embodiment of the invention using a clip or tie.
Figure 2B:
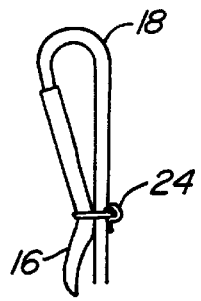
Figure 2C:
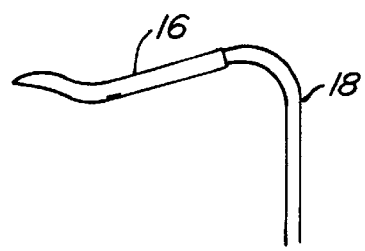

FIGS. 2A–2C illustrate one embodiment of the invention. FIG. 2A illustrates one embodiment of a sensor having a sensor or sensor head portion 16 connected to a sensor rod 18. In the embodiment shown, the sensor has a fulcrum 20 for biasing the sensor head against the fetus' head, so that a light emitter and detector 22 is forced up against the fetus' head.

FIG. 2B illustrates sensor rod 18 being bent around a greater than 180° angle, with the sensor head 16 being secured in position with a tie 24. Alternately, a clip, sleeve or any other securing device could be used. The sensor as shown in FIG. 2B can then be placed into normal packaging for shipment, and when the package is opened, tie 24 can be removed. FIG. 2C illustrates the plastic memory of sensor rod 18 maintaining a bent angle of approximately 90° after tie 24 has been removed.

Preferably, the sensor rod is bent around 180 degrees, plus or minus 30 degrees, or between 150 and 210 degrees. However, smaller or larger angles could be used in alternate embodiments.

Figure 3:
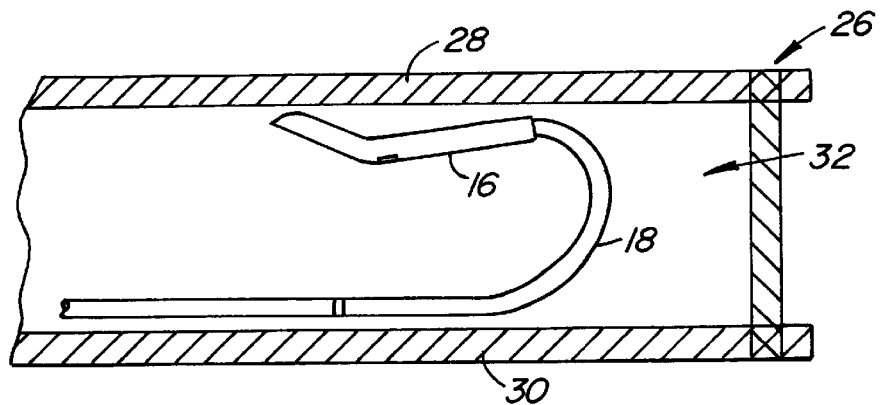
FIG. 3 is a diagram illustrating an embodiment of the invention using narrow packaging to restrain the sensor.

FIG. 3 illustrates an alternate embodiment of the invention showing sensor rod 18 being bent before insertion into a package 26. Package 26 includes seals 28 and 30 which form a cavity 32 which is sufficiently narrow so that sensor rod 18 is enclosed and restrained in a bent position as shown. Upon removal from package 26, rod 18 will straighten somewhat, but still maintain a partial bend, similar to the bend illustrated in FIG. 2C. Alternately, a smaller package may be used to restrain the sensor in its bent condition; with the smaller package then being inserted into the final package for shipping.

Figure 4:
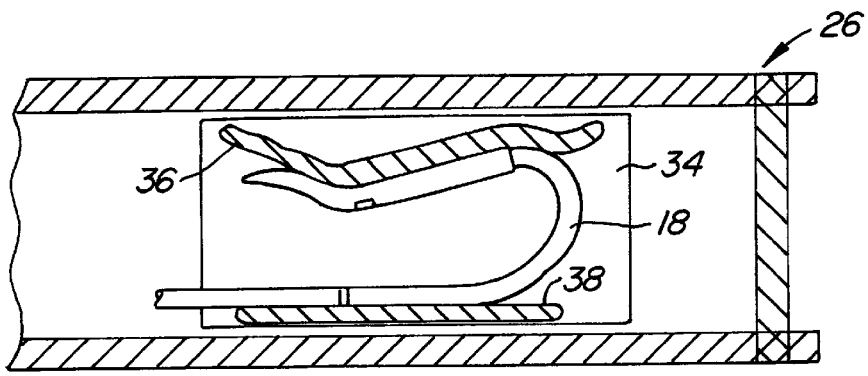
FIG. 4 is a diagram of an alternate embodiment using a preformed tray to hold the sensor.

FIG. 4 shows an alternate embodiment of the invention in which sensor rod 18 is bent and held in place by a tray 34 which includes preformed ridges 36 and 38 for restraining the sensor in the curved position. Tray 34 can then be inserted into plastic packaging 26 for shipment. Upon removal, sensor rod 18 will expand to the bent position shown in FIG. 2C. Alternately, instead of using a tray 34, the package 26 itself could simply have seals at the positions shown for ridges 36 and 38.

Figure 5:
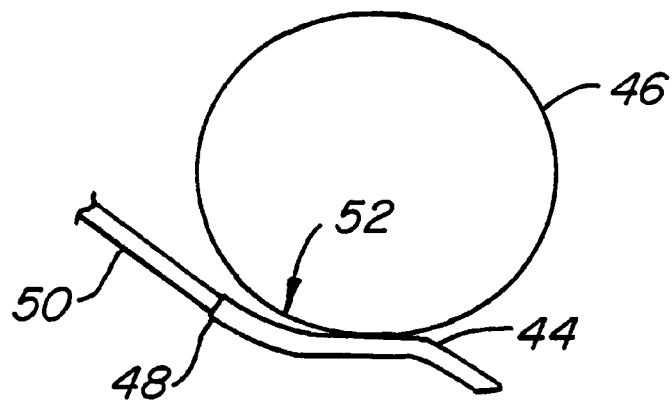
FIG. 5 is a diagram of an alternative embodiment using a curved overmold to maintain the sensor rod in a curved position.

FIG. 5 shows an embodiment with a sensor head 44 against a fetus' head 46. The overmold material of the sensor head is extended, in a curved path, to a position 48 over sensor rod 50. This allows sensor rod 50 to be manufactured with an extrusion process, with a limited molding over the sensor rod inducing the desired curve. The length of the overmold could be approximately doubled, for example, from approximately 3 inches to up to 6 inches, for instance, to accomplish the curve. The curve desirably has a radius less than that of a typical fetus at term, for instance one half the radius, so that there will be a biasing action against the fetus. Alternately, a radius approximately equal to that of the fetus' head could be used to have the sensor follow the shape of the fetus' head, but not be biased against it by the curved rod. Instead, the biasing against the fetus' head is accomplished by a fulcrum, bladder, or other apparatus at the distal end of the sensor.

Figure 6:
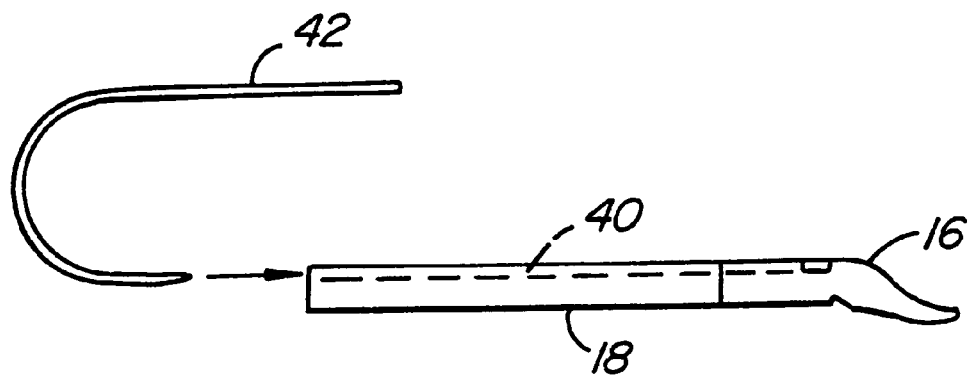
FIG. 6 is a diagram illustrating the use of a curved stylet to bend the sensor.

FIG. 6 illustrates yet another embodiment of the invention in which sensor rod 18 is shown having an internal channel 40 for insertion of a stylet. A curved stylet 42 is inserted into channel 40, to bend sensor rod 18. The sensor can then be shipped, and upon removal and preparation for use, bent stylet 42 is removed and discarded. The sensor will maintain a bent shape similar to that shown in FIG. 2C.

In use, the sensor of FIG. 6, or the sensors of any of the embodiments shown above, can have a metal stylet inserted to straighten out the sensor for insertion into a uterus. After insertion and placement, the metal stylet can be removed, with the sensor returning to the bent position to bias it around the fetus' head as desired.

The steel, or other material, stylet used for straightening can be packaged while it is inserted into the sensor, if the steel is hard enough so that the curve does not plastically deform the stylet. In the embodiment of FIG. 5, the steel stylet would either have to be removed, or the channel would have to be sufficiently large to accommodate both the steel stylet and the curved stylet 42.

If a stylet is used which would bend after being held in a curved position for a period of time, the stylet would have to be removed either partially, so that it does not extend into the bent portion of the sensor rod, or totally removed and placed alongside the sensor in the packaging. In one embodiment, the sensor rod is a cable jacket made of a plastic material such as Santoprene®, a thermoplastic elastomer.

As will be understood by those of skill in the art, the present invention may be embodied in other specific forms without departing from the spirit or essential characteristics thereof. For example, the sensor could be bent through less than 180°, or could be restrained by a loose loop rather than a tight clip or tie. Accordingly, the foregoing description is intended to be illustrative, but not limiting, of the scope of the invention which is set forth in the following claims.

What is claimed is:

1. A method for packaging an oximeter sensor having a sensor rod connected to a sensor, comprising the steps of:

forming said sensor rod from a material which has memory;

bending said sensor rod more than amount of desired bending;

restraining said sensor rod in a bent position with a restraining material; and packaging and shipping said sensor;

such, that after being shipped said sensor can be unpacked and will expand to a partially bent position upon removal of said restraining material.

2. The method of claim 1 wherein said restraining step comprises securing a portion of said oximeter sensor near a distal end to a mid-portion of said sensor rod.

3. The method of claim 1 wherein said restraining step comprises enclosing said oximeter sensor with packaging material.

4. The method of claim 3 wherein said enclosing step comprises placing said oximeter sensor in a surrounding package sufficiently narrow to maintain said sensor in said bent position.

5. The method of claim 1 wherein said sensor rod includes a channel for inserting a stylet, and said restraining step further comprises inserting a curved stylet into said channel.

6. The method of claim 1 wherein said oximeter sensor is bent around approximately a 180 degree angle.

7. The method of claim 1 wherein said oximeter sensor is bent around at least a 150 degree angle.

8. The method of claim 1 wherein said sensor rod includes a channel for inserting a stylet, and further comprising the step of only partially inserting said stylet so that it is not bent when said sensor rod is bent.

9. The method of claim 1 wherein said sensor rod is bent between 150 and 210 degrees and is made of a plastic having a plastic memory sufficient to retain a bend of between 45 and 120 degrees after unrestraining said sensor rod.

10. The method of claim 9 wherein said plastic is a thermoplastic elastomer.

11. A method for packaging an oximeter sensor having a sensor rod connected to a sensor, wherein said sensor rod includes a channel for inserting a stylet, comprising the steps of:

forming said sensor rod from a material which has memory;

only partially inserting said stylet so that it is not bent when said sensor rod is bent;

bending said sensor rod more than the amount of desired bending;

restraining said sensor rod in a bent position with a restraining material;

wherein said sensor rod is bent between 150 and 210 degrees and is made of a plastic having a plastic memory sufficient to retain a bend of between 45 and 120 degrees after unrestraining said sensor rod; and packaging and shipping said sensor;

such that after being shipped said sensor can be unpacked and will expand to a partially bent position upon removal of said restraining material.

* * * * *